US012673162B2

(12) United States Patent
   Bruns et al.

(10) Patent No.:  US 12,673,162 B2
(45) Date of Patent:      Jul. 7, 2026

(54) AUTO-INJECTOR

(71) Applicant: Owen Mumford Limited, Woodstock (GB)

(72) Inventors: Robert William Bruns, Woodstock (GB); Paul McPherson, Woodstock (GB)

(73) Assignee: OWEN MUMFORD LIMITED, Oxfordshire (GB)

( * ) Notice: Subject to any disclaimer, the term of this patent is extended or adjusted under 35 U.S.C. 154(b) by 1346 days.

(21) Appl. No.: 17/278,968

(22) PCT Filed: Sep. 27, 2019

(86) PCT No.: PCT/EP2019/076318
   § 371 (c)(1),
   (2) Date: Mar. 23, 2021

(87) PCT Pub. No.: WO2020/065073
   PCT Pub. Date: Apr. 2, 2020

(65) Prior Publication Data
   US 2022/0023542 A1     Jan. 27, 2022

(30) Foreign Application Priority Data
   Sep. 28, 2018   (GB) ...................................... 1815829

(51) Int. Cl.
   *A61M 5/20*       (2006.01)
   *A61M 5/32*       (2006.01)
(52) U.S. Cl.
   CPC ........ *A61M 5/2033* (2013.01); *A61M 5/3204* (2013.01); *A61M 2005/202* (2013.01);
   (Continued)

(58) Field of Classification Search
   CPC .... A61M 5/2033; A61M 5/3204; A61M 5/20; A61M 5/24; A61M 5/28; A61M 5/3129;
   (Continued)

(56) References Cited

U.S. PATENT DOCUMENTS

| | | | |
|---|---|---|---|
| 4,681,566 A | 7/1987 | Fenton, Jr. et al. | |
| 6,099,503 A | 8/2000 | Stradella | |

(Continued)

FOREIGN PATENT DOCUMENTS

| | | |
|---|---|---|
| CN | 101678171 B | 9/2012 |
| CN | 102307609 B | 8/2013 |

(Continued)

OTHER PUBLICATIONS

International Search Report from corresponding International Application No. PCT/EP2019/076318, mailed Jan. 8, 2020, (5 pages).
(Continued)

*Primary Examiner* — Kevin C Sirmons
*Assistant Examiner* — Alexandra Lalonde
(74) *Attorney, Agent, or Firm* — QUARLES & BRADY LLP

(57)        ABSTRACT

An injection device comprising a housing to house a syringe, an activation member, a drive mechanism to, upon activation by the activation member, drive a plunger driver between a first position and a second position to operate the syringe within the housing and a damping mechanism configured to damp movement of the plunger driver in either a forward motion or a rearward motion. The plunger position may affect an amount of travel of the plunger driver before it is in contact with the plunger and the plunger is in contact with a drug within a barrel. During travel, a drive force may cause rapid acceleration of the plunger driver, and damage to the syringe or discomfort to an injection recipient when contact between the plunger driver, the syringe, and the recipient is
(Continued)

made. Damping of the forward motion of the plunger driver reduces or overcomes the risk of this.

7 Claims, 10 Drawing Sheets

(52) U.S. Cl.
CPC .............. *A61M 2005/2026* (2013.01); *A61M 2005/206* (2013.01); *A61M 2005/2086* (2013.01)

(58) Field of Classification Search
CPC ........ A61M 5/31511; A61M 2005/202; A61M 2005/2026; A61M 2005/206; A61M 2005/2086; A61M 2005/3152; A61M 2005/3143; A61M 2005/2418; A61M 2005/3131; A61M 2005/31516
See application file for complete search history.

(56) References Cited

U.S. PATENT DOCUMENTS

| | | | |
|---|---|---|---|
| 6,270,479 B1 * | 8/2001 | Bergens | A61M 5/2033 604/156 |
| 2010/0137808 A1 | 6/2010 | Wilmot et al. | |
| 2011/0028910 A1 * | 2/2011 | Weber | A61M 5/2033 604/211 |
| 2013/0138048 A1 | 5/2013 | Kemp | |
| 2013/0138049 A1 | 5/2013 | Kemp et al. | |

| | | | |
|---|---|---|---|
| 2013/0296795 A1 | 11/2013 | Ekman et al. | |
| 2013/0317446 A1 | 11/2013 | Hourmand et al. | |
| 2014/0336589 A1 | 11/2014 | Sund et al. | |
| 2015/0290392 A1 | 10/2015 | Henderson et al. | |
| 2015/0297833 A1 | 10/2015 | Henderson et al. | |
| 2016/0346476 A1 | 12/2016 | Cappello et al. | |

FOREIGN PATENT DOCUMENTS

| | | |
|---|---|---|
| CN | 103998076 B | 6/2016 |
| CN | 106535966 A | 3/2017 |
| CN | 107345548 A | 11/2017 |
| CN | 103656796 B | 2/2018 |
| CN | 104768594 B | 3/2018 |
| CN | 107816503 A | 3/2018 |
| CN | 108025137 A | 5/2018 |
| CN | 105900162 B | 10/2018 |
| CN | 105682706 B | 2/2019 |
| EP | 2080532 B1 | 12/2010 |
| EP | 2399631 A1 | 12/2011 |
| EP | 2727617 A1 | 5/2014 |
| TW | 201818987 A | 6/2018 |
| WO | 03097133 A1 | 11/2003 |
| WO | 2011012849 A1 | 2/2011 |
| WO | 2018082887 A1 | 5/2018 |

OTHER PUBLICATIONS

Written Opinion of the International Searching Authority from corresponding International Application No. PCT/ EP2019/076318, dated Jan. 8, 2020 (7 pages).

* cited by examiner

C

AUTO-INJECTOR

CROSS-REFERENCE TO RELATED APPLICATIONS

The present application represents the United States National Stage of International Application No. PCT/EP2019/076318, filed Sep. 27, 2019, which relates to and claims priority to British Patent Application Serial No. GB 1815829.5, filed Sep. 28, 2018, both of which are incorporated herein by reference in their entirety.

TECHNICAL FIELD

The present disclosure relates to an injection device. In particular, it relates to an injection device where movement of a plunger driver is damped.

BACKGROUND

Often the delivery of a medicament is automated with the user performing an action to cause the medicament to be delivered without any further action by them. Auto-injectors to provide medicament in this way include, or can receive, a syringe. Syringes typically comprise a barrel to receive medication; a needle end with a needle, or means to receive a needle; and a plunger at the other end. When the plunger of the syringe is depressed it moves towards the needle end of the syringe causing medicament to be ejected from the syringe.

Auto-injectors typically include a plunger driver to drive the plunger of the syringe towards the needle end of the syringe. The plunger driver may be driven towards needle by a drive spring. The drive spring and driver may be activated by operation of a button or trigger, or movement of the shroud.

SUMMARY OF THE INVENTION

According to an aspect of the invention there is provided an injection device comprising a housing configured to house a syringe, an activation member, a drive mechanism configured to, upon activation by the activation member, drive the plunger driver between a first, initial, position and a second, final, position thereby to operate the syringe within the housing and a damping mechanism configured to damp movement of the plunger driver in either a forward or rearward motion. In this way, tolerances in plunger position may be accounted for. Plunger position may affect the amount of travel of the plunger driver before the plunger driver is in contact with the plunger and the plunger is in contact with the drug within the barrel. During this travel, the drive force may cause rapid acceleration of the plunger driver, which may then cause damage to the syringe or discomfort to the recipient of the injection when contact between the three elements is made. Damping of the forward motion of the plunger driver reduces or overcomes the risk of this.

The damping mechanism may be configured to damp an initial portion of the motion of the plunger driver.

The damping mechanism is configured to damp motion of the plunger driver from the first position to the second position i.e. from the primed position to the position in which all the drug has been delivered. This helps to reduce shock effects and wear on the components of the auto-injector, increasing their life.

The damping mechanism may be configured to damp rearward movement of the plunger driver. This prevents the door snapping shut if released during opening and priming of the drive mechanism.

The damping mechanism may be a rotary damper or a linear damper.

The damping mechanism may be a rack and pinion arrangement wherein rotation of the pinion is damped in at least one direction. The pinion may be coupled to the plunger driver and the rack may be coupled to the housing. The rack may extend along a portion of the housing at and/or adjacent to the first position thereby to damp the initial portion of motion of the plunger driver. Alternatively, or additionally there may be provided a rack to extend along a portion of the housing at and/or adjacent to the second position thereby to damp the final portion of motion of the plunger driver. Optionally, the rack may extend between the first position and the second position thereby to damp the full region of motion of the plunger driver after activation.

Rotation of the pinion may be damped such that motion of the plunger driver is damped when it is moving from the first position to the second position and not damped when the plunger driver is moving from the second position to the first position. This reduces the energy or force required to move the plunger driver back to the primed position in which it can deliver medicament in a syringe.

The damping mechanism comprises a friction means to impart friction on the plunger driver. The friction means may comprise a surface having one or more different frictional coefficients, the surface being situated such that it is in contact with the plunger driver and/or a component coupled to the plunger driver at least during motion of the plunger driver from the first position to the second position. The surface co-efficient may vary gradually at one or more point in order to enable a gradual increase in damping on the plunger driver removing any sudden forces that may be applied to the plunger damper. The surface may have an area of greater frictional co-efficient at and/or adjacent to the first position thereby to damp the initial portion of motion of the plunger driver. The surface may have an area of greater frictional co-efficient at and/or adjacent to the second position thereby to damp the final portion of motion of the plunger driver.

The friction means comprises a friction area and a recess, wherein the friction area is in contact with the plunger driver and/or a component coupled to the plunger driver at least during motion of the plunger driver from the first position to the second position and the recess provides no friction to the plunger driver and/or the component coupled to the plunger driver during motion of the plunger driver from the first position to the second position.

The friction means may be moveable between a position in which it damps movement of the plunger driver and/or a component coupled to the plunger driver as it moves between the first position and the second position and a position in which it does not damp movement of the plunger driver and/or a component coupled to the plunger driver as it moves between the first position and the second position. For example, the friction surface may be provided on the door of the device.

The damping mechanism may comprise a damping arm pivotally mounted within the housing in a position in which it contacts the plunger driver as the plunger driver moves from the first position to the second position. In addition to the damping arm the damping mechanism may also include a resetting arm, pivotally mounted within the housing, in a position in which it contacts the plunger driver as the plunger driver moves from the second position to the first position, the damping arm and resetting arm being coupled such that rotation of one causes rotation of the other. The damping arm and the resetting arm may be coupled perpendicular to one another. Rotation of the damping arm is damped when rotation of the damping arm is caused by contact with the plunger driver and not damped when rotation of the damping arm is caused by rotation of the resetting arm.

BRIEF DESCRIPTION OF THE DRAWINGS

One or more embodiments of the invention will now be described, by way of example only, with reference to the accompanying drawings, in which.

DETAILED DESCRIPTION

Generally, disclosed herein are exemplary methods and apparatus for auto-injectors and in some specific arrangements, safety auto-injectors. The term "auto-injector" is used herein and may be considered to encompass both an auto-injector and a safety auto-injector, as appropriate. The auto-injectors may be configured to receive and operate a standard syringe (i.e. not a safety syringe) and/or a safety syringe. A syringe is generally comprised of a barrel containing a medicament. At a forward end of the syringe is a needle or a means to receive a needle. At a rearward end of the syringe there is provided a plunger. The plunger is generally made of an elastomeric material and application of pressure on the plunger causes the medicament contained within the syringe to be ejected from the syringe via the needle.

Although the auto-injectors described herein are reusable auto-injectors it will be understood that the methods described below are also applicable to single use auto-injectors where the plunger driver may not be reactivated. They are also applicable to any injection device where delivery of a medicament is automated and not manual.

In the following embodiments, the terms "forward" and "front" refer to the patient facing end of the injection device or component thereof. In other words, the front end of the injection device is the end proximal to the injection site during use. Likewise, the term "rear" refers to the non-patient end of the injection device assembly or component thereof. In other words, the term "rear" means distant or remote from the injection site during use. Further, the term longitudinal is used to encompass a direction along or parallel to a longitudinal axis of the injection device.

Features of the exemplary arrangements disclosed herein are described as being "coupled" to other features. This term encompasses any coupling that results in the coupled features moving together in any direction, whether that be on a 1:1 basis or on some geared basis. The term "coupled" also encompasses any one of a connection between features, an abutment of one feature against another and an engagement of one feature with another, and such coupling may be direct or may be indirect, i.e. with a third feature therebetween.

Figure 1A:
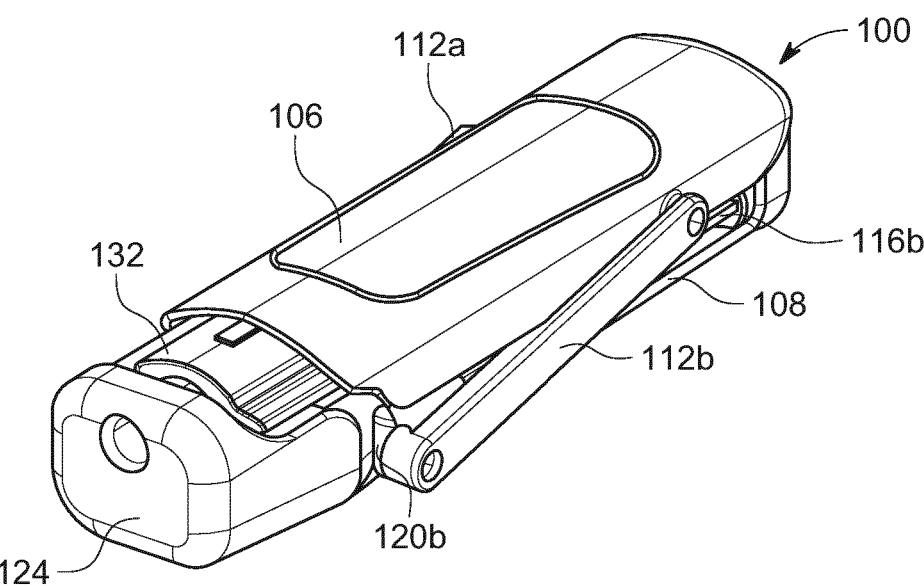
FIGS. 1a and 1b show perspective views of an auto-injector.
Figure 1B:
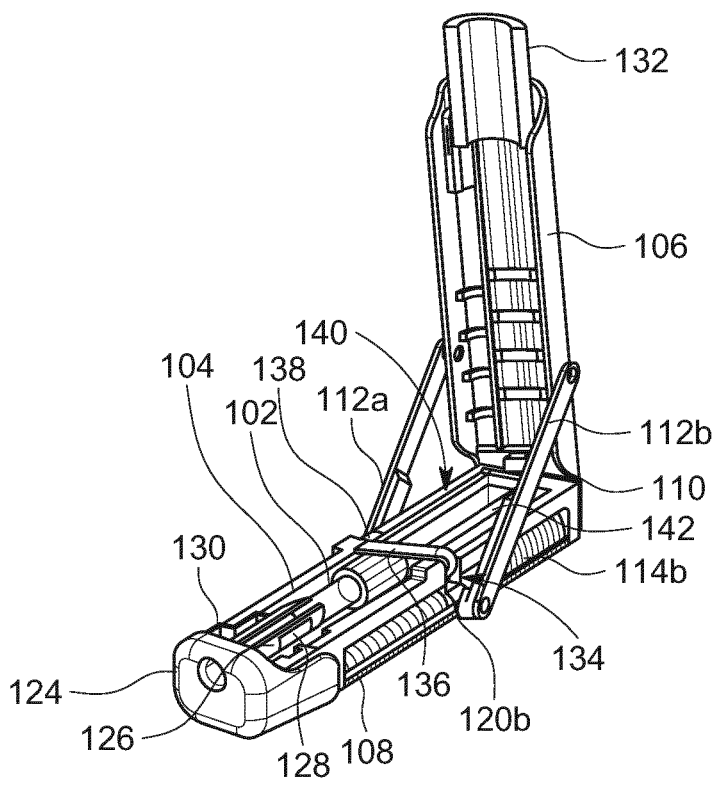

FIGS. 1a and 1b show an exemplary auto-injector 100 for receiving and operating a syringe 102. The auto-injector comprises a housing that further comprises a plurality of component parts. In the example of FIGS. 1a and 1b, the housing comprises a main body 104, a hinged door 106 (termed "door" herein) and in some exemplary arrangements, a rear body 108. FIG. 1a shows the auto-injector 100 with the door 106 in a closed position and FIG. 1b shows the auto-injector 100 with the door 106 in an open position. The door 106 is operable between these two positions. As can be seen, the syringe 102 may be received within the housing, and in this case specifically in the main body 104, when the door 106 is in the open position. The door 106 may comprise a hinged connection 110 with the main body 104.

Two charging links 112a, 112b connect the door 106 to the main body 104. Connections between the charging links 112a, 112b and the main body 104 and/or between the door 106 and the charging links 112a, 112b are slidable. This allows opening of the door 106 about the hinged connection 110. In the example shown in FIGS. 1a and 1b, the connection between the charging links 112a, 112b and the main body 104 is slidable.

The auto-injector 100 further comprises at least one drive spring and in the case of FIGS. 1a and 1b two drive springs 114a, 114b (drive spring 114a not shown in FIGS. 1a and 1b but located in a similar position to drive spring 114b on the opposite side of the auto-injector 100). The sliding connections of the charging links 112a, 112b to the main body 104 are configured to couple to the drive springs 114a, 114b to prime them by compression thereof on opening of the door 106. It will be apparent to the skilled person that other arrangements are possible such as priming the drive springs 114a, 114b on closing of the door 106.

The auto-injector 100 also comprises a spring guide 116a, 116b (spring guide 116a not shown in FIGS. 1a and 1b but located in a similar position to spring guide 116b on the opposite side of the auto-injector 100), which in the example shown in FIGS. 1a and 1b comprise rods. The rods have a cross-shaped cross section. The rods comprise a reaction surface 118a, 118b against which a rearward end of the drive springs 114a, 114b is placed. Extension of the drive springs 114a, 114b therefore produces a force acting in a forward direction.

The drive springs 114a, 114b are located about the rods such that the rods pass through an aperture defined by the drive springs 114a, 114b. In this way, extension and compression of the drive springs 114a, 114b follows the path defined by the spring guides 116a, 116b. The skilled person will appreciate that other forms of spring guide may be used.

The slidable connections of the charging links 112a, 112b may be provided by charging linkages 120a, 120b. The charging linkages 120a, 120b are rotationally connected to the charging links 112a, 112b and configured to slide along the spring guides 116a, 30 116b. In the case of FIGS. 1a and 1b, the charging linkages 120a, 120b comprise an aperture though which the spring guides 116a, 116b (e.g. rods) pass.

The auto-injector 100 also comprises two plunger drivers 122a, 122b, but these are not easily seen in FIGS. 1a and 1b and can best be seen in later figures, where their operation is fully described. Broadly, the plunger drivers 122a, 122b are connected or otherwise coupled to an end of the drive springs 114a, 114b such that extension of the drive springs 114a, 114b drives the plunger drivers 122a, 122b forwards. The plunger drivers 122a, 122b are arranged to contact a plunger of the syringe 102, thereby driving that forwards and operating the syringe 102.

The auto-injector 100 also comprises a shroud. In the exemplary arrangement of FIGS. 1a and 1b, the shroud comprises a main body portion 130 and a door portion 132. The main body portion 130 is slidably connected to the main body 104. The door portion 132 is slidably connected to the door 106. Therefore, and as shown in FIG. 1b, when the door 106 is in the open position, the shroud is split. This allows the syringe 102 to be loaded into the auto-injector 100 from the top without the need to thread the needle end of the syringe 102 through the shroud. The main body portion 130 and the door portion 132 also comprise keying features that are configured to interlock when the door 106 is in the closed position. This longitudinally couples the main body portion 130 to the door portion 132, which can then move together longitudinally. A shroud spring biases the shroud in a forward direction.

The main body 104 comprises one or more recessed areas that represent a "ghosted" impression of the syringe 102. For example, the main body may comprise a recess 134 for receiving a handle portion 136 and finger flanges 138 of the syringe 102. Further, the main body 104 may comprise a recess 140 for receiving an extended plunger assembly 142 of the syringe 102. The recess 140 may have a length that accounts for tolerances in plunger position of prefilled syringes.

Figure 2A:
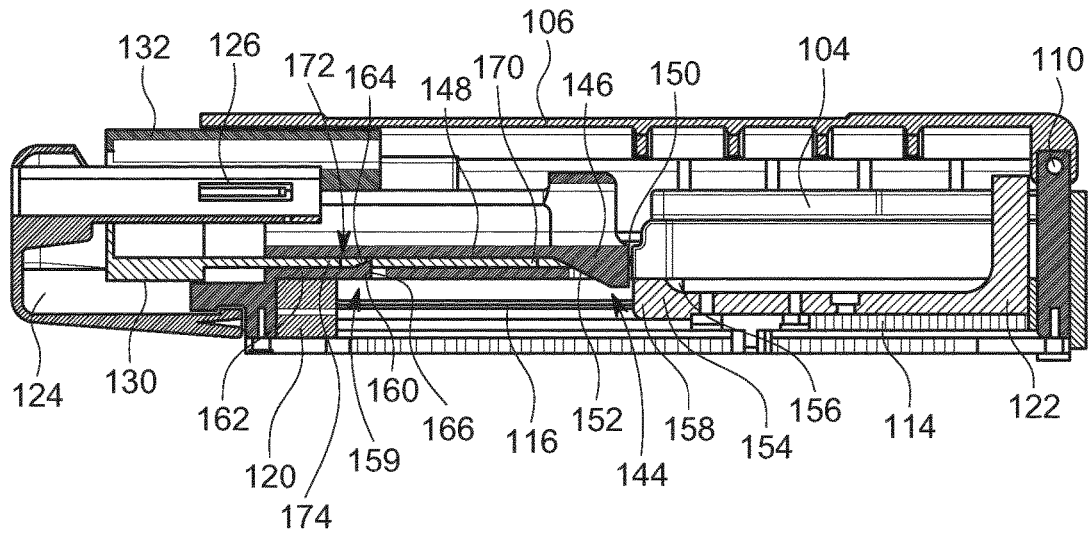
FIG. 2a shows a section through an auto-injector.
Figure 2B:
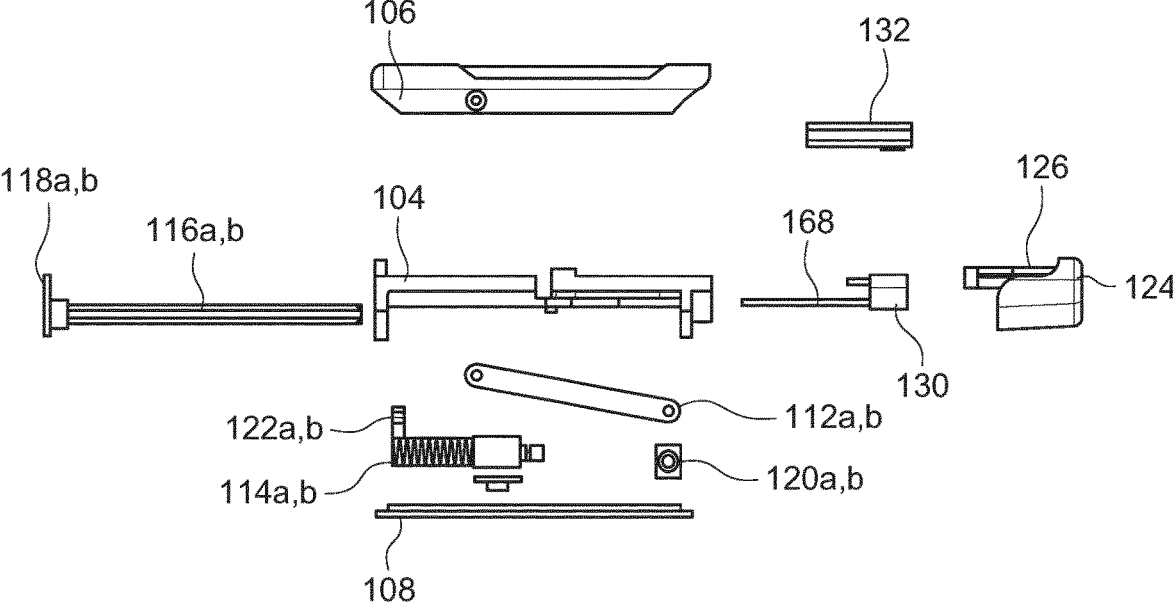
FIG. 2b shows an exploded view of an auto-injector.

FIGS. 2a and 2b show a section through the auto-injector 100 and an exploded view of the auto-injector 100 respectively. Many of the features already discussed in respect of FIGS. 1a and 1b are also shown in FIGS. 2a and 2b.

Referring to FIGS. 2a and 2b, the main body 104 comprises one or more driver latches 144. For the remainder of this part of the description, reference will be made to features on one side of a longitudinal axis of the auto-injector 100. However, the same features and associated description may be relevant to the opposite side of the longitudinal axis. The driver latch 144 is configured to prevent forward motion of the plunger driver 122. The driver latch 144 comprises a projection 146 that extends transverse to the longitudinal axis from a resiliently deformable arm 148. The projection 146 comprises a rearward facing latching surface 150 and a forward facing angled surface 152 extending laterally from a direction of the resiliently deformable arm 148. In a resting position of the resiliently deformable arm 148, the projection is in a path followed by the plunger driver 122 under the influence of the drive spring 114. The plunger driver 122 comprises a projection 154 extending transverse to the longitudinal axis of the auto-injector. The projection 154 comprises a rearward facing angled surface 156 and a forward facing abutment surface 158. The abutment surface 158 is arranged to abut the latching surface 150 when the plunger driver 122 is retained by the driver latch 144.

The main body 104 also comprises a sheath latch 159 comprising a projection 160 projecting transverse to a resiliently deformable prong 162 and to a longitudinal axis of the auto-injector 100. The projection 160 comprises a rearward facing angled surface 164 and a forward facing latching surface 166. The shroud, and in the exemplary arrangement of FIGS. 1-2, the main body portion 130 of the shroud, comprises a rearward extending latch release arm 168. Rearward movement of the shroud and therefore the latch release arm 168 is configured to release the driver latch 144. In the example shown in the figures, this is achieved by a drive release surface 170. As explained below, the drive release surface 170 rides over the rearward facing angled surface of the driver latch 144 to release the driver latch 144 and allow forward movement of the plunger driver 122.

The latch release arm 168 also comprises an aperture or recess 172 in which the projection 160 of sheath latch 159 is received before operation of the auto-injector 100. This represents the resting position of the resiliently deformable prong 162. In the resting position of the prong 162, the projection 160 is out of the path of the plunger driver 122, which is therefore allowed to pass. A rear surface (or sheath release surface) 174 of the aperture 172 is configured to engage the latch by riding over the angled surface 164 of the projection 160 on rearward movement of the shroud. Subsequent forward movement of the shroud allows the projection 160 to re-enter the aperture 172 under force of the prong 162, thereby releasing the latch.

Figure 3:
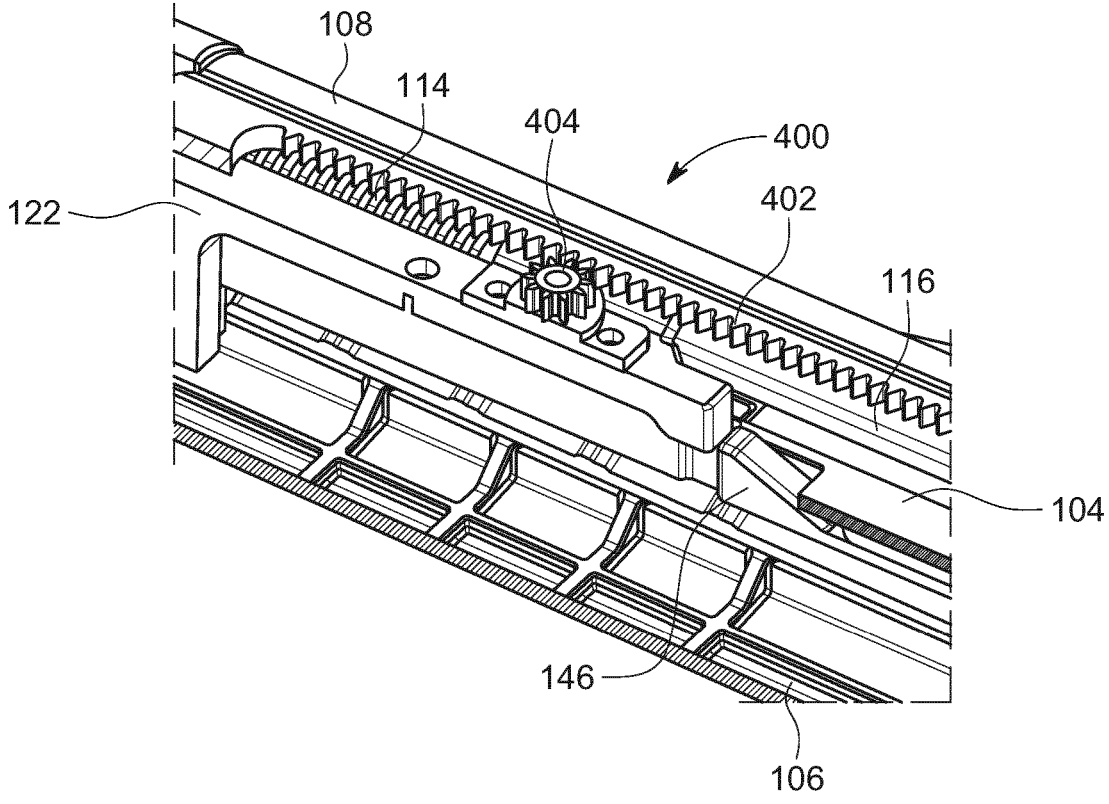
FIG. 3 shows an exemplary damper for an auto-injector.

FIG. 3 shows an exemplary damper 400 fitted to the auto-injector 100. The damper 400 may be configured to damp forward and/or rearward motion of the plunger driver 122. In one example, the damper 400 is configured to damp at least an initial phase of the forward motion of the plunger driver 122. This initial phase may be up to 15 mm, up to 10 mm or up to 5 mm. In this way, tolerances in plunger position may be accounted for. Plunger position may affect the overall length of the auto-injector 100 and/or the amount of travel of the plunger driver 122 before the plunger driver is in contact with the plunger and the plunger is in contact with the drug within the barrel. During this travel, the spring force may cause rapid acceleration of the plunger, which may then cause damage to the syringe or discomfort to the recipient of the injection when contact between the three elements is made. Damping of the forward motion of the plunger driver 122 reduces or overcomes the risk of this.

The damper 400 may also be configured to operate over more of the forward travel of the plunger driver 122, and in some arrangement may operate over the full forward travel of the plunger driver. This reduces shock effects and wear on the components of the auto-injector, increasing their life.

Further, the damper 400 may damp rearward travel of the plunger driver 122. This prevents the door 106 snapping shut if released during opening and priming of the drive spring 114.

In FIG. 3, the exemplary damper 400 comprises a rack 402 and pinion 404 arrangement. The pinion 404 is connected to the plunger driver and travels along the rack 402 with movement of the plunger driver 122 forwards or backwards. The pinion 404 is configured to have damped rotation in one or both direction for damping travel of the plunger driver 122.

Figure 4A:
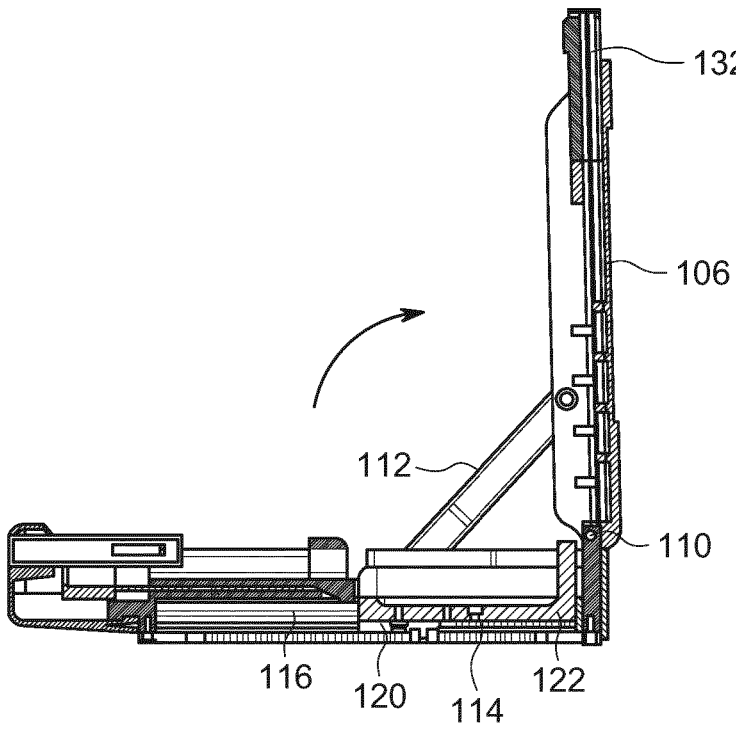
FIGS. 4a-4g show sections through an auto-injector at various stages of operation.

Operation of the auto-injector is now described with reference to FIGS. 4a-4g. In FIG. 4a, the hinged door 106 is opened about the hinged connection 110. This slides the charging linkage 120 of the charging link 112 along the spring guide 116. In cases where the door 106 is opened after operation of the device, the drive spring 114 will be extended along the spring guide 116 before opening. Therefore, the charging linkage 120 couples (in this case abuts) to the drive spring 114 during opening of the door 106. The lever action of the door 106 allows the user to gain a mechanical advantage in priming the drive spring 114. This may be a particular advantage when high force springs are used, for example when a drug to be delivered by the auto-injector has a high viscosity. In some examples, the viscosity of the drug may be in a range from 12 centipoise (cP) to 18 cP, in a range from 14 cP to 16 cP, or may be 15 cP. Further, the drug may need to be delivered through a 29 gauge thin wall needle, although other gauge needles may be used. This requires a relatively high spring force, for example 40N to 50 N and may be 45 N, which a user may find difficult to prime.

During opening of the door 106, the charging linkage 120 compresses the drive spring 114 and moves the plunger driver 122 rearwards. The rearward facing angled surface 156 of the plunger driver 122 contacts the forward facing angled surface 152 of the driver latch 144 and displaces the projection 146 laterally allowing the plunger driver 122 to pass. After the plunger driver 122 has passed, the projection 146 springs back into the path of the plunger driver 122 under force of the resilient arm 148. The plunger driver 122 is therefore latched.

The door portion 132 moves with the door 106, thereby allowing the syringe 102 to be received into the auto-injector laterally without the need to thread the needle end through the shroud.

Figure 4B:
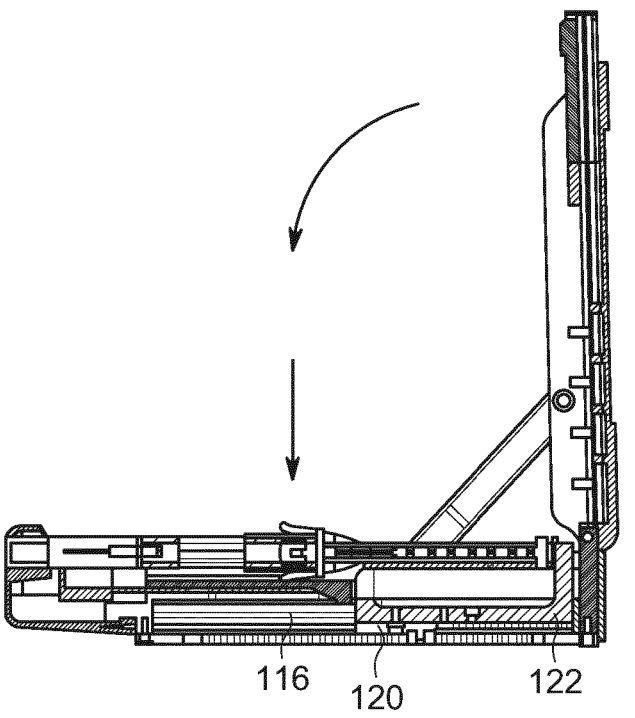

In FIG. 4*b*, the syringe 102 is inserted into the main body 104 using the ghosting recesses 134, 140 and the receiving tray 126. The door 106 is then closed about the hinged connection 110. The charging linkage 120 slides forwards along the spring guide 116. The plunger driver 122 is retained by the driver latch 144 and the drive spring 114 does not expand along the spring guide 116. There is therefore room on the spring guide 116 into which the drive spring 114 can expand on operation of the auto-injector 100. The door portion 132 of the shroud connects to the main body portion 130 of the shroud via the keying features such that the two are longitudinally coupled or connected.

Figure 4C:
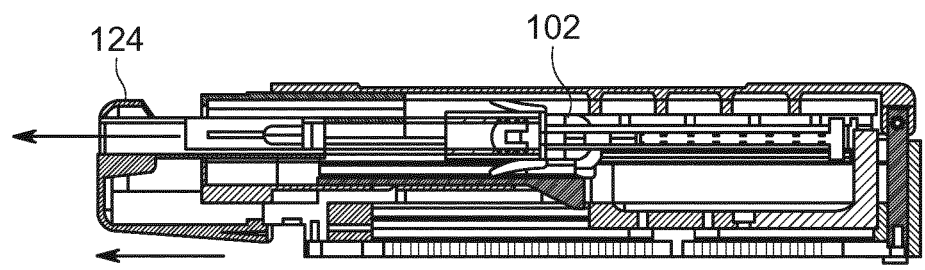

FIG. 4*c* shows the cap 124 being removed. The deformable prongs 128 of the receiving tray 126 catch on the RNS of the syringe 102, which is therefore also removed. The cap 124 comprises an aperture through which the RNS drops after removal from the needle.

Figure 4D:
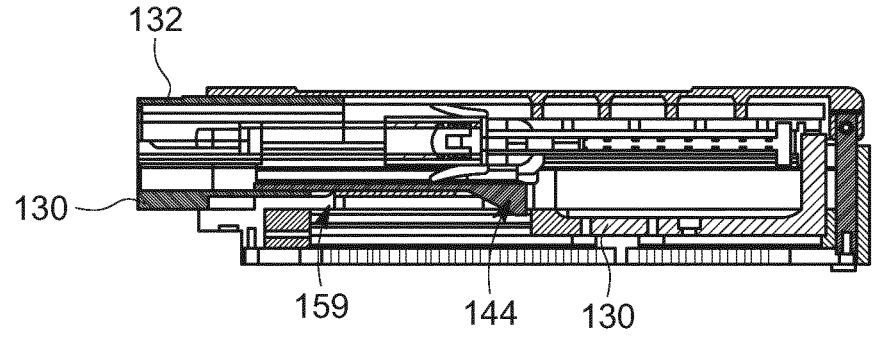

As can be seen in FIG. 4*d*, the main body portion 130 and the door portion 132 of the shroud surround the needle and extend beyond the forward end of the needle, which is therefore shielded. The shroud is biased in a forward direction under force of a shroud spring. The driver latch 144 is engaged and therefore is in the path of the plunger driver 122. Further, the sheath latch 159 is received with the aperture 172 of the latch release arm 168 and is out of the path of the plunger driver 122.

Figure 4E:
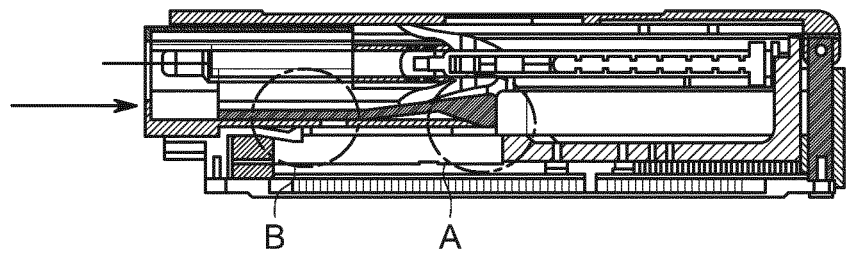
Figure 4F:
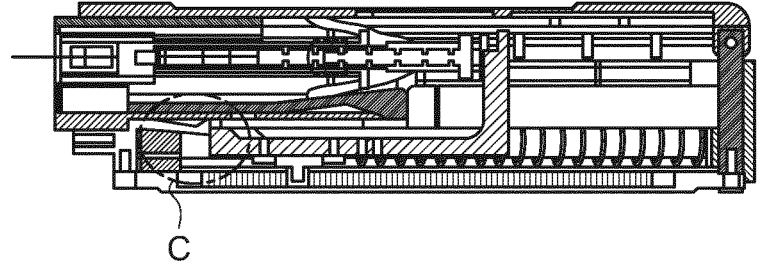

In FIG. 4*e* the shroud is pushed rearwards into the auto-injector 100. This may be done by a user pressing the shroud against an injection site. This action exposes the needle, which enters the injection site. In other arrangements, the syringe 102 may be moved forward within a syringe carrier under force of a spring. In such arrangements, rearward movement of the shroud (or indeed the depression of a button) may release the spring to drive the syringe carrier forwards for needle insertion.

The forward facing drive release surface 170 of the latch release arm 168 rides over the rearward facing angled surface of the projection 146 of the driver latch 144. This displaces the projection 146 laterally out of the path of the plunger driver 122 (to the left in FIG. 4*e*). This action can be seen in the circle A of FIG. 4*e*. Also, rearward movement of the shroud causes the sheath release surface 174 of the aperture 172 in the latch release arm 168 rides over the rearward facing angled surface 164 of the projection 160 of the sheath latch 159. This displaces the projection 160 laterally into the path of the plunger driver 122 (to the right in FIG. 4*e*). This action can be seen in the circle B.

Disengagement of the driver latch 144 releases the drive spring 114, which drives the plunger driver forwards and thereby drives the plunger of the syringe 102 into the barrel. This forces the plunger further into the barrel and dispenses the drug (or other substance) from the syringe 102. In some arrangements, movement of the plunger driver 122 may be damped, in particular during an initial phase of a forward stroke. This is described below in more detail.

The plunger driver 122 is driven forwards until it reaches the sheath latch 159, which is now engaged and in the path of the plunger driver 122. The sheath latch 159 therefore halts progress of the plunger driver 122. The sheath latch 159 may be positioned such that the plunger 122 driver is halted at a point on the forward stroke at which the full dose of drug has been delivered from the barrel or at a point afterwards. The exemplary arrangement shown in the figures is configured for use with a safety syringe in which further movement of a plunger after full dose delivery deploys a sheath to protect the needle after use of the syringe 102. Therefore, halting forward motion of the plunger driver 122 prevents deployment of the sheath. It will be appreciated that sheaths of safety syringes may also be deployed under force of a separate spring that may be released by a sheath release mechanism. Such a mechanism may be released by forward movement of the plunger (or plunger driver 122) after full dose delivery. Such arrangements are encompassed within embodiments disclosed herein.

Figure 4G:
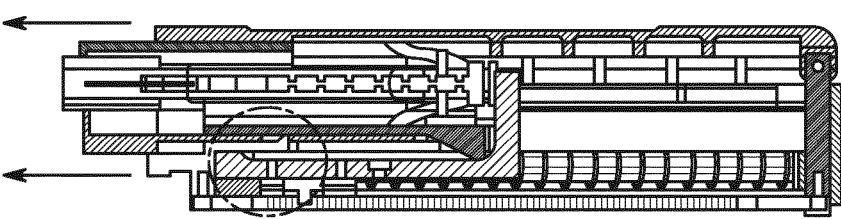

After full dose delivery, the user lifts the auto-injector away from the injection site. The shroud is therefore urged forwards under the force of the shroud spring, which is shown in FIG. 4*g*. Forward movement of the shroud causes forward movement of the latch release arm 168 until the aperture 172 is longitudinally aligned with the projection 160. The projection 160 therefore enters the aperture 172 under force of the prong 162. This disengages the sheath latch 159 and moves the projection 160 out of the path of the plunger driver 122 allowing forward movement thereof. Further forward movement of the plunger driver 122 causes further forward movement of the plunger of the auto-injector 100, thereby deploying the sheath. The door 106 can now be opened, priming the drive spring 114 again and allowing removal of the sheathed safety syringe 102.

In some arrangements, a plurality of drive springs 114 may be located on the autoinjector 100. One or more of the plurality of drive springs 114 may be configured to be in an active or a passive state. That is, one or more of the drive springs 114 may be configured either to contribute to driving the plunger driver 122 forwards or not to contribute to driving the plunger driver 122 forwards. Configuration may comprise removing one or more of the drive springs 114 from the auto-injector 100. This may be done during assembly of the auto-injector 100. In other arrangements, a setting on the auto-injector may configure the one or more drive springs 114. For example, one of the charging links 112 may be disconnected from the door 106. The drive spring described above comprises two tension springs, however, the skilled person will understand that the drive spring may be any other suitable biasing member. Including, but not limited to a tension spring, a compression spring or a torsion spring.

FIGS. 5*a* to 6*b* show perspective views of an alternative auto-injector for receiving and operating a syringe (not shown). In these Figures like features operate as described with reference to FIGS. 1 to 4 unless otherwise indicated. Like features have maintained the same final two digits of the reference number.

As described previously the auto-injector 500 comprises a drive spring 514. The drive spring 514 is configured to drive a plunger of a syringe received within the auto-injector 500 forwards to dispense a fluid from the syringe.

The auto-injector 500 further comprises at least one biaser 509 configured to bias the hinged door 506 towards the primed position. As described below, the biaser 509 assists the priming of the drive spring 514 of the auto-injector 500 by providing an assisting force to help a user move the hinged door 506 to its primed position, ready for firing.

Figure 5A:
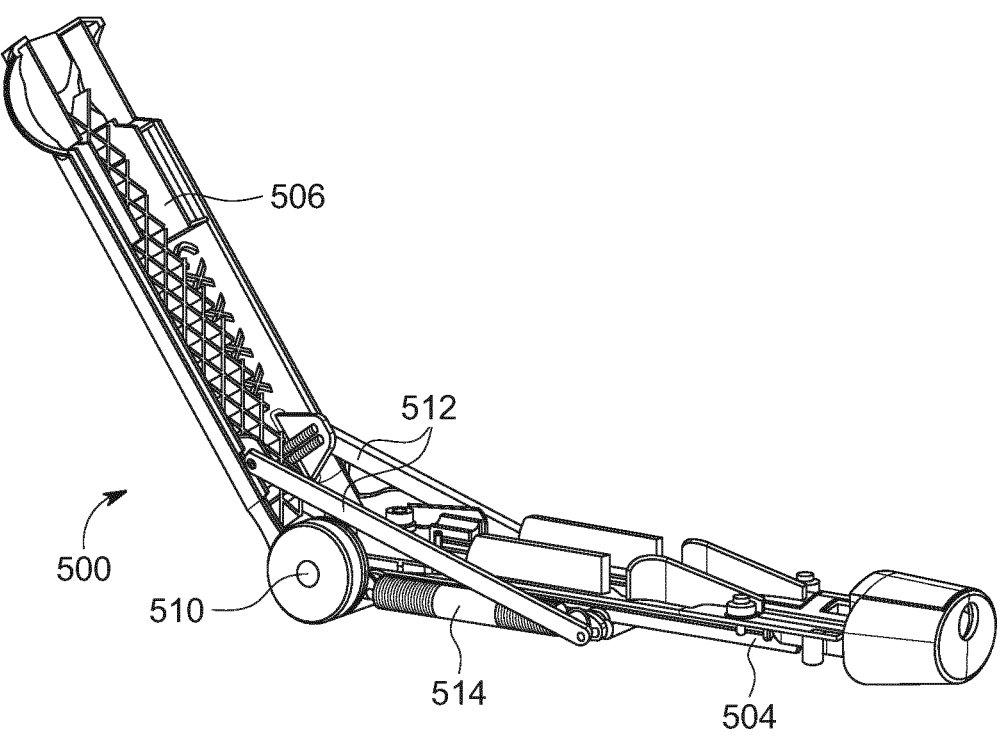
FIGS. 5a-5b show perspective views of an alternative auto-injector.
Figure 5B:
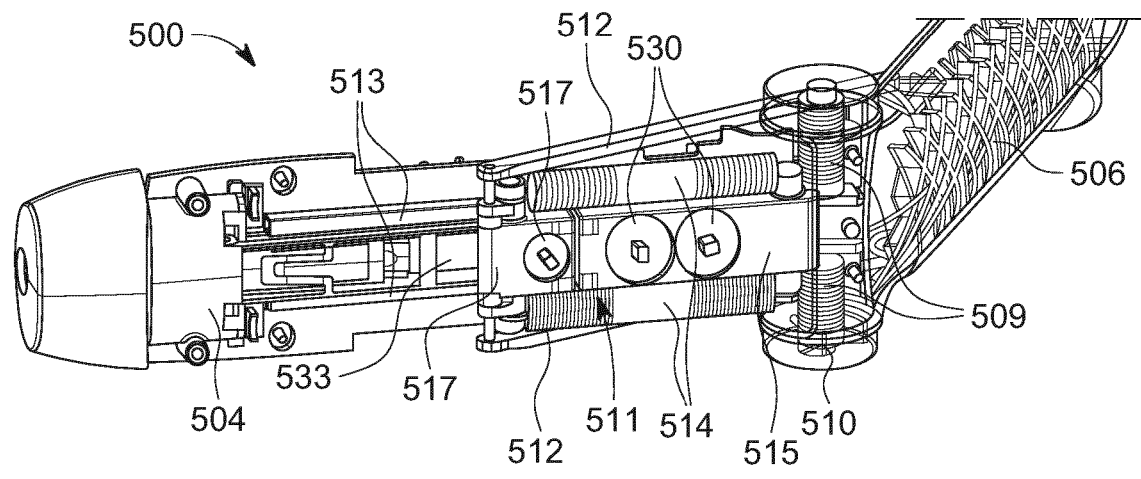
Figure 5C:
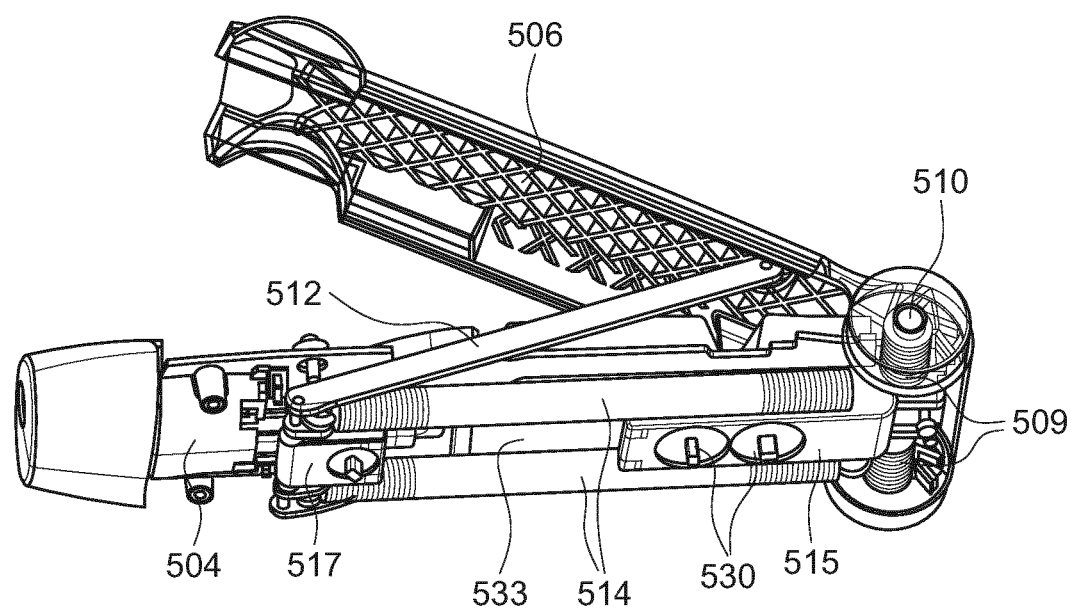
FIG. 5c shows a perspective view of the alternative auto-injector undergoing priming.

The biaser 509 may comprise one or more springs, which may be tension springs, compression springs, torsion springs or other types of spring. In the example of FIGS. 5a and 5b, the biaser 509 comprises two torsion springs coupled to the hinged door 506 and to the main body 504 about the hinged connection 510. Relative movement between the hinged door 506 and the main body 504 about the hinge 103 twists the torsion springs on opening and/or closing movement of the hinged door 506. In the example of FIGS. 5a and 5b, opening the hinged door 506 to load a syringe into the auto-injector 500 primes the torsion springs. The torsion springs 509 are primed when the hinged door 506 is in the unprimed position. The torsion springs act on the hinged door 506 to apply a torque to bias the hinged door 506 towards its primed position (in this case the closed position).

In the example of FIGS. 5a and 5b, opening the hinged door 506 translates the drive spring 514 rearwardly without priming it. The opening movement of the hinged door 506 thus permits a syringe to be loaded into the auto-injector 500 before priming. Before closing of the hinged door 506, an end of the tension springs of the plunger driver is retained in position relative to the main body 504. On closing the hinged door 506, which is rotatably connected to the charging link 512, is pushed in a forwards direction. In turn, the charging link 512, through its slidable connection to the main body 504 and because it is coupled to an opposite end of the tension springs, slides along the main body 504 and thereby extends the tension springs of the drive spring 514, as is shown later in FIG. 5c.

Each charging link 512 may be coupled to a shuttle 511. The shuttle 511 may be slidable along the main body 504 and configured to travel along a shuttle guide 513. The shuttle guide 515 may be the same as the spring guide 116 described previously or may be provided as a separate component. The charging link 512 and the shuttle 511 are connected, the connection may be rotatable. In some arrangements, the shuttle 511 provides the slideable connection of the charging link 512 to the main body 504.

The shuttle 511 comprises a first priming portion 515 and a second priming portion 517. The drive spring(s) 514 are connected between the first and second priming portions 515, 517. The first and second priming portions 515, 517 are configured to travel along the shuttle guide 515 together towards the hinged connection when the door 516 is open as shown in FIG. 5b. As the drive spring(s) 514 are connected between the first and second priming portions 515, 517, this movement does not prime the drive spring 514.

Figure 6A:
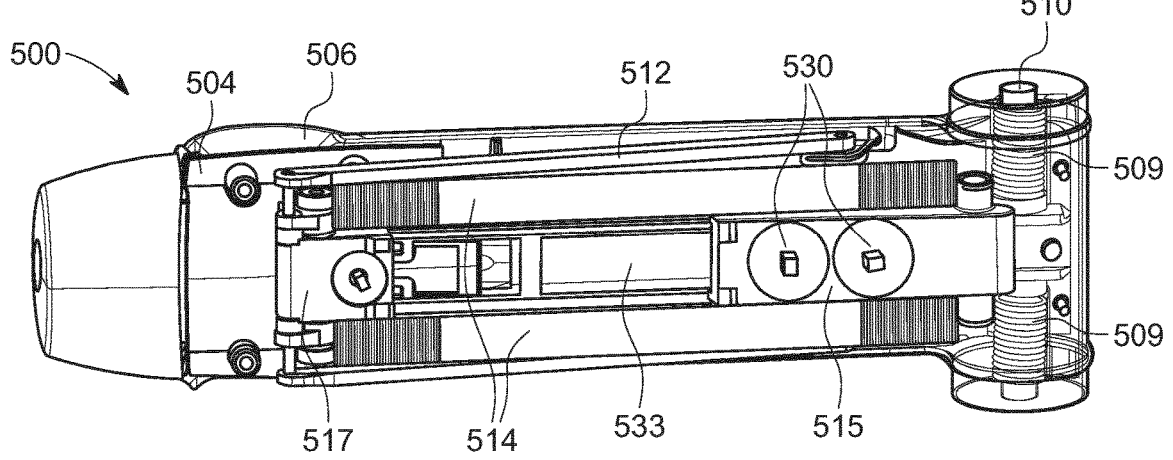
FIG. 6a shows a perspective view of the alternative auto-injector after priming.

The main body 504 and/or the first priming portion 515 may comprise a latch configured to retain the first priming portion 515 in position on the shuttle guide 513 after opening of the hinged door 506. The first and second priming portions 515, 517 are separable after opening of the hinged door 506. The second priming portion 517 is configured to travel along the shuttle guide 513 away from the hinged connection 510 on closing of the door 506 as shown in FIG. 6a. Because the drive spring(s) 514 are connected between the first and second priming portions 515, 517, as the second priming portion 517 travels forward the drive spring(s) 514 are primed ready to provide a delivery force to the plunger driver and thus deliver medication from the syringe.

As described above, the first and second priming portions 515, 517 are configured to travel together along the shuttle guide 513 on opening of the door 506, and are separable such that the second priming portion 517 separates from the first priming portion 515 and travels along the shuttle guide 513 on closing of the door 506. This separated state is shown in FIG. 6a.

FIG. 6a shows a view of the underside of the auto-injector 500 in a primed state with the hinged door 506 closed and the drive spring 514 primed. The drive spring 514 is retained in its primed state by latch retaining the first priming portion 515 in position. In the example of FIG. 4a, the drive spring 514 comprises two tension springs which are fully extended.

Figure 6B:
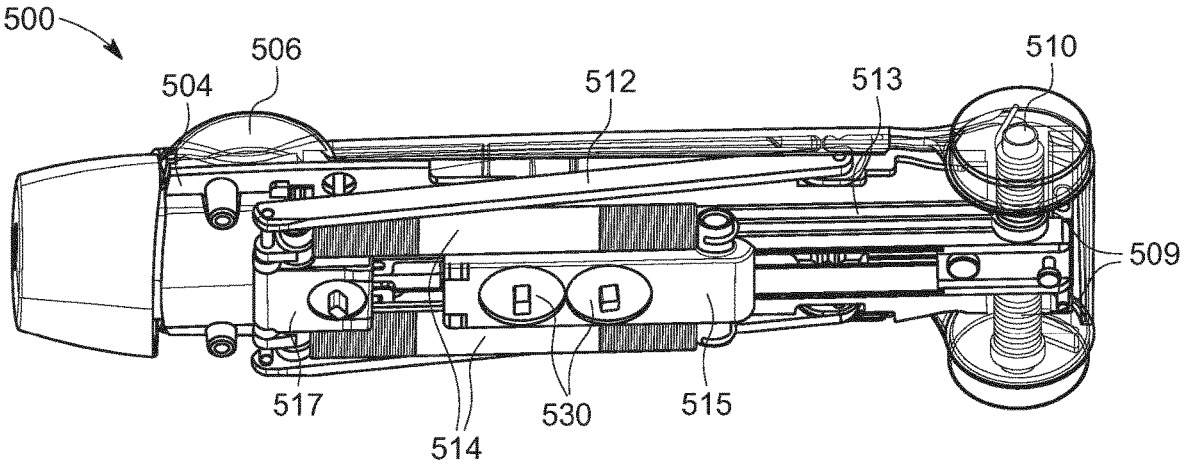
FIG. 6b shows a perspective view of the alternative auto-injector during activation.

FIG. 6b shows a perspective view of the underside of the auto-injector 500 during activation. The drive spring 514 is configured, on activation to drive a plunger driver forward within the auto-injector 500 to operate the syringe received with the auto-injector 500. In the example of FIG. 6b, the tension springs work together to provide the forward force necessary to cause a drug in the mounted syringe to be injected into a patient. The plunger driver may be coupled to the drive springs 514 to achieve this.

The first priming portion 515 is provided with two pinions 530. The skilled person will understand that the number of pinions may depend on a number of factors and therefore any number of pinions may be provided, including one. The pinions are located on a rack (not shown) such as that shown in FIG. 3 previously. The rack is located on the main body 504 for example in the aperture 533 that can be seen in FIG. 5a.

The pinions 530 are connected to the drive spring 514 via the first priming portion 515. When the auto-injector is activated, as shown in FIG. 6b, the drive spring 514 moves forward in the auto-injector. As the first priming portion 515 is coupled to the drive spring it also travels along the rack with movement of the drive spring. As the first priming portion 515 moves forward the pinion moves along the rack thereby damping the forward motion of the plunger driver (not shown) by the drive spring 514.

As will be understood by the skilled person the rack illustrated in FIG. 3 or as described with reference to FIGS. 5a to 6b may be present either over the entire length of travel of the plunger driver. Alternatively, the rack may be present along a part of the main body corresponding to an initial portion of movement of the plunger driver or the final portion of movement of the plunger driver.

Damping of the initial portion of movement of the plunger driver acts to reduce the rate of acceleration of the plunger driver resulting in the plunger driver contacting the plunger with less force than if the plunger driver had not been damped. This facilitates, for example, the use of syringes having different plunger positions. For example, a syringe having a plunger further away from the needle end of the syringe will be contacted when the plunger driver is moving at a low speed as the plunger driver is still accelerating. In contrast a syringe having a plunger near the needle end will be contacted when the plunger driver is moving at terminal velocity requiring a large amount of force to be dissipated when the plunger driver's speed is retarded by contacting the plunger. By using a damper, such as that described above, the increase in the plunger driver's speed is retarded and thus, the force to be dissipated when the plunger meets the plunger is reduced.

Damping the final portion of the movement of the plunger driver may be useful decelerate the speed of the plunger driver before the plunger contacts the end of the syringe. This increases the ability of the auto-injector to supply all of the medicament contained within the syringe as it allows the plunger to be driven the entire length of the syringe while reducing the force with which the plunger meets the syringe end. This facilitates the use of medicaments having different viscosities as the plunger will meet the end of the syringe at a higher velocity when the medicament has a lower viscosity than when it has a higher viscosity. By reducing the velocity that the plunger meets the end of the syringe the force that it meets the end of the syringe is reduced.

Optionally, the pinion may be configured to have damped rotation in one or both direction for damping travel of the plunger driver. By reducing rearward motion of the plunger driver wear on components within the auto-injector is reduced.

Although the present invention has been described with reference to a rack and pinion damping mechanism the skilled person will understand that any suitable linear and/or rotary damper may be used.

In another example the damping may be provided by providing areas of greater friction to retard the motion of the plunger driver. For example, the areas of friction may be provided on areas of the shuttle guide 513. The area of friction being configured to retard the acceleration of the first priming portion 515 once the auto-injector is activated. Alternatively the areas of friction may replace all or a portion of the track described previously with the plunger driver being provided with means to contact the areas of friction.

The areas of friction may be, for example, provided on a track that the plunger driver, or a component coupled to the plunger driver is in constant access to. In this instance the areas may be provided with an elastomeric material and the areas which are not areas of friction provided with a surface having a lower frictional co-efficient then the areas of friction. Alternatively, the track may be such that the plunger driver, or a component coupled to the plunger driver is only in contact with the track when damping is desired. For example, the track may comprise a recess when no damping is desired. The areas of the track may be provided with any suitable surface to provide the retardation of acceleration required. For example, as described previously the surface of the track may be provided with an elastomeric material such as rubber.

The frictional surface may be able to be moved away from the plunger driver or component coupled to the plunger driver when the plunger driver is being moved to a primed position in order to reduce the effort required to move the plunger driver to a position where it can be activated again. This may be achieved, for example, by mounting the frictional surface on the door of the device or by rotating the surface away from the plunger driver or component.

Figure 7A:
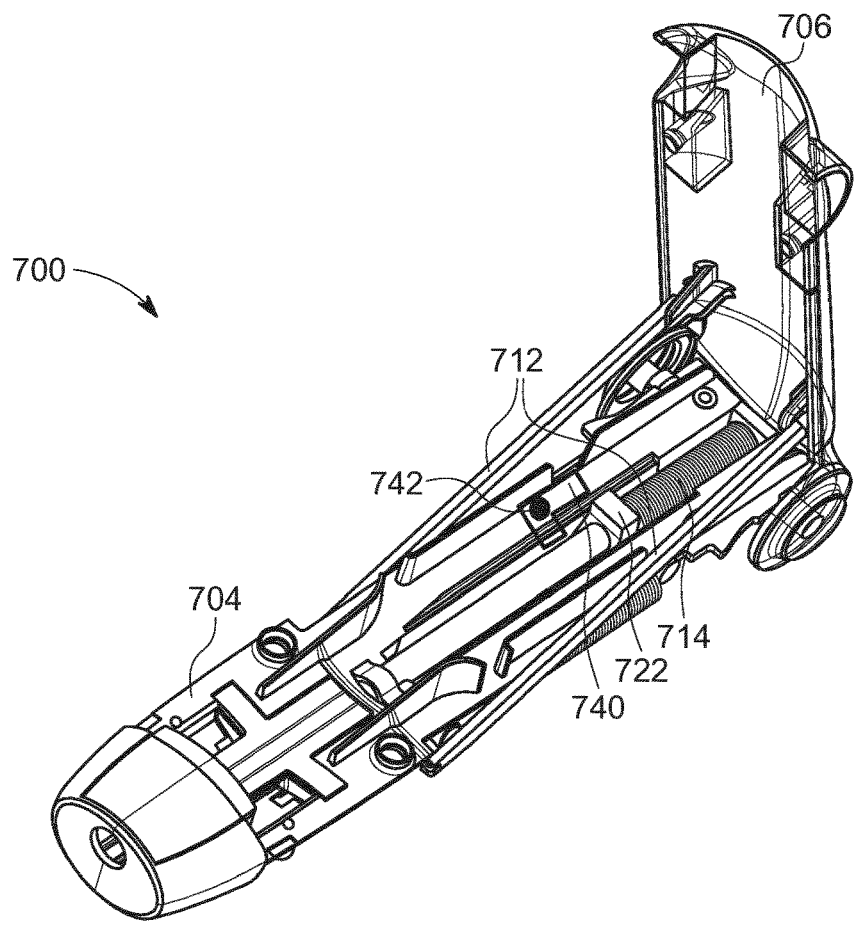
FIGS. 7a and 7b show perspective views of another auto-injector.
Figure 7B:
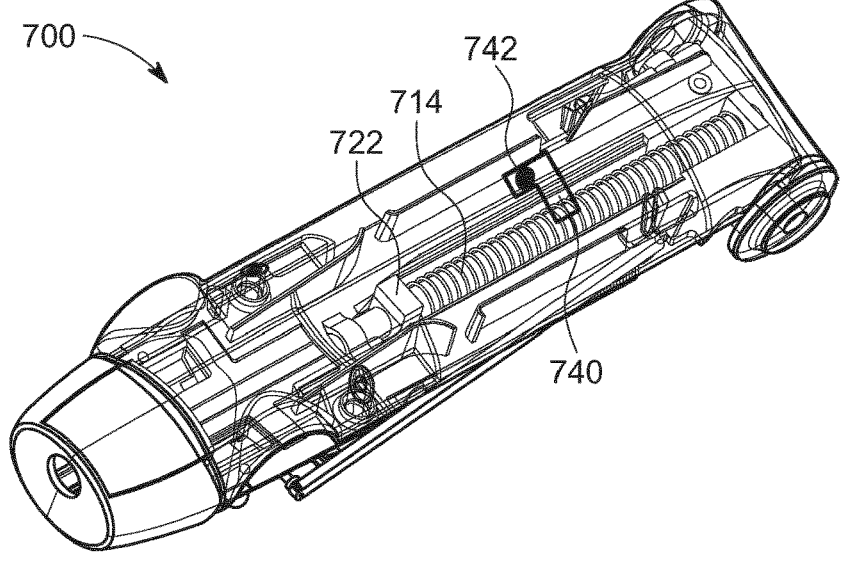

In yet another example, as illustrated in FIGS. 7 and 7*b*, acceleration of the plunger driver is retarded by mechanical means. In these Figures like features operate as described with reference to FIGS. 1 to 6 unless otherwise indicated. Like features have maintained the same final two digits of the reference number. FIGS. 7*a* and 7*b* illustrate an auto-injector 700, comprising a hinged door 706 and charging links 712.

FIG. 7*a* illustrates the drive spring 714 and plunger driver 722 in a pre-delivery configuration where the drive spring 714 is primed. FIG. 7*b* shows the position of the drive spring 714 and plunger driver 722 after the auto-injector has been activated. In the configuration shown in FIGS. 7*a* and 7*b* damping of the movement of the plunger driver 722 is achieved using a mechanical member 740 comprising two perpendicular arms and a coupling member 742. The coupling member connects the mechanical member to the main body 704 and provides a pivot point about which the two perpendicular arms can rotate.

On activation of the auto-injector the plunger driver 722 moves between the position shown in FIG. 7*a* to the position shown in FIG. 7*b*. As the plunger driver moves forward it contacts the one of the two perpendicular arms that project across its pathway. The plunger driver contacting the arm causes the mechanical member to pivot about the coupling member 742 to the position shown in FIG. 7*b*. Contact of the plunger driver 722 with the arm of the mechanical member retards the acceleration of the plunger driver. The acceleration may be retarded further if the rotation of the arms about the coupling member is damped.

When the device is to be reprimed the plunger driver is moved back to a position in which it can drive a plunger down a syringe i.e. when the plunger driver 722 is moved from the position shown in FIG. 7*b* to the position shown in FIG. 7*a*. During this movement the plunger driver contacts the other of the arms rotating the mechanical member about the coupling member back to its original position. Thereby resetting the mechanical member and enabling it to damp the forward motion of the plunger driver when the auto-injector is next activated. The rotation of the mechanical member may be damped only in the direction of rotation caused by the plunger driver moving forward in the auto-injector and not in the direction of rotation caused when the plunger driver is moved rearward in the auto-injector. This means that no additional force is required when resetting the auto-injector.

In the event that the auto-injector is not a reusable auto-injector and therefore the plunger driver does not need to be moved back to the position shown in FIG. 7*a* it will be understood that the mechanical member 740 may only have a single arm positioned to damp the forward motion of the plunger driver.

Although the present invention has been described with reference to a hinged door it may be understood that other door configurations are possible. For example the main body and door may have a slideable connection.

The skilled person will be able to envisage other assemblies, auto-injectors and features thereof without departing from the scope of the appended claims. In particular, it is noted that one or more features included in one or more drawings may be integrated into auto-injectors shown in other drawings, as will be appreciated by the skilled person. It should be understood that the detailed description and specific examples are given by way of illustration only, since various changes and modifications within the spirit and scope of the disclosure will become apparent to those skilled in the art from the description.

The invention claimed is:

1. An injection device comprising:
    a. a housing configured to house a syringe;
    b. an activation member;
    c. a drive mechanism configured to, upon activation by the activation member, drive a plunger driver between a first, initial, position and a second, final, position thereby to operate the syringe within the housing;

d. a damping mechanism configured to damp movement of the plunger driver in a forward motion and a rearward motion, wherein the damping mechanism comprises an arrangement which comprises a rack and a pinion, wherein the pinion is coupled to the plunger driver and the rack is fixedly coupled to the housing in an axial direction at all times during operation of the injection device, and wherein the rack and the pinion are configured to damp the forward motion and the rearward motion of the plunger driver.

2. The injection device as claimed in claim 1, wherein the damping mechanism is configured to damp an initial portion of the forward motion of the plunger driver.

3. The injection device as claimed in claim 1, wherein the damping mechanism is configured to damp the forward motion of the plunger driver from the first, initial, position to the second, final, position.

4. The injection device according to claim 1, wherein the rack extends along a portion of the housing at and/or adjacent to the plunger driver when the plunger driver is in the first, initial, position thereby to damp an initial portion of the forward motion of the plunger driver.

5. The injection device according to claim 1, wherein the rack extends along a portion of the housing at and/or adjacent to the plunger driver when the plunger driver is in the second, final, position thereby to damp a final portion of the forward motion of the plunger driver.

6. The injection device according to claim 1, wherein the rack extends between a location of the plunger driver in the first, initial, position and a location of the plunger driver in the second, final, position thereby to damp a full region of the forward motion or the rearward motion of the plunger driver after the activation.

7. The injection device as claimed in claim 1, wherein the housing is further configured to house the activation member, the drive mechanism, the plunger driver, and the damping mechanism.

* * * * *